United States Patent

Ohyama et al.

Patent Number: 5,929,104
Date of Patent: Jul. 27, 1999

[54] METHOD FOR INDUCING APOPTOSIS OF CANCER CELL

[75] Inventors: Harumi Ohyama, Chiba; Takeshi Yamada, Funabashi; Yoshiya Furusawa, Narashino; Atsuko Kamohara, Hiratsuka; Mizuho Saito, Chiba, all of Japan

[73] Assignee: Pola Chemical Industries, Inc., Shizuoka, Japan

[21] Appl. No.: 08/829,879

[22] Filed: Apr. 2, 1997

[51] Int. Cl.$^6$ ............. A61K 31/415; A61K 31/70; A61K 31/505; A61K 33/24
[52] U.S. Cl. ............. 514/399; 514/400; 514/34; 514/274; 424/649
[58] Field of Search ............. 514/399, 400, 514/392, 34, 274; 424/649

[56] References Cited

FOREIGN PATENT DOCUMENTS 0 312 858 A1  4/1989  European Pat. Off. ......... 514/292
WO91/11440   8/1991  WIPO ......................... 514/292

OTHER PUBLICATIONS

Seg–Lasley et al., Manual of Oncology Therapeutics, C.V. Mosby Co., St Louis pages 88&104, 1981.
Sakakura et al., *Int. J. Cancer*, 67, 101–105 (1996).
Adams et al., *Radiation Research*, 67, 9–20 (1976).
Phillips et al., *Cancer*, 48, 1697–1704 (1981).
Saito et al., Report of the 9th Annual Meeting of The Japanesse Society foor Therapeutic Radiation and Oncology (Jastro), with translation.

*Primary Examiner*—Jerome D. Goldberg
*Attorney, Agent, or Firm*—Bacon & Thomas

[57] ABSTRACT

Disclosed herein are a method for inducing apoptosis of cancer cells, which comprises administering an effective amount of a 2-nitroimidazole derivative represented by the general formula (1):

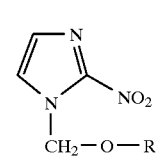

(1)

wherein R represents an alkyl, alkenyl or alkynyl group substituted by 1 to 3 hydroxyl groups, and a method for treating a cancer, which comprises using the method for inducing apoptosis in combination with another means for killing cancer cells.

6 Claims, 2 Drawing Sheets

METHOD FOR INDUCING APOPTOSIS OF CANCER CELL

BACKGROUND OF THE INVENTION

1. Field of the Invention

The present invention relates to induction of apoptosis by a 2-nitroimidazole derivative, and more particularly to a method for inducing apoptosis of cancer cells by this compound to treat a cancer.

2. Description of the Background Art

Medical treatments for cancers are roughly divided into radiotherapy and chemotherapy. In recent years, induction of apoptosis of cancer cells has been known to be an important factor for treatment of cancers in both radiotherapy and chemotherapy. An attempt to treat a cancer by inducing apoptosis of cancer cells is going to be performed.

On the other hand, 2-nitroimidazole derivatives represented by the following general formula (1):

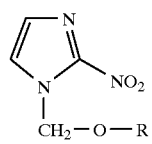

(1)

wherein R represents an alkyl, alkenyl or alkynyl group substituted by 1 to 3 hydroxyl groups, have been already known to be useful for cancer radiotherapy as radiosensitizing agents for hypoxic cells (EP 312858, WO91/11440). As described in Whillans, D. W. et al., Radiat. Res. 62(3), 407–421 (1975), the radiosensitizing effect of these compounds on the hypoxic cells is said to be based on the mechanism that these compounds distribute toward the hypoxic cells, which generate oxygen radical to only a small extent by irradiation because they are hypoxic, and their nitro group reoxygenates the hypoxic cells to enhance the radiosensitivity of the hypoxic cells. However, what action these compounds exert on apoptosis of cancer cells has not been known at all.

SUMMARY OF THE INVENTION

Accordingly, the present inventor has carried out an extensive investigation as to various effects of the 2-nitroimidazole derivatives (1) on cancer cells. As a result, it has been unexpectedly found that these compounds have an effect of inducing apoptosis of the cancer cells and are particularly useful in treatment for cancers by using them in combination with other means for killing cancer cells, thus leading to completion of the present invention.

In an aspect of the present invention, there is thus provided a method for inducing apoptosis of cancer cells, which comprises administering an effective amount of a 2-nitroimidazole derivative represented by the general formula (1):

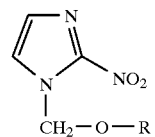

(1)

wherein R represents an alkyl, alkenyl or alkynyl group substituted by 1 to 3 hydroxyl groups.

In another aspect of the present invention, there is also provided a method for treating a cancer, which comprises using the method for inducing apoptosis making use of the 2-nitroimidazole derivative (1) in combination with another means for killing cancer cells.

Features and advantages of the present invention will be readily appreciated from the preferred embodiments of the present invention, which will be described subsequently in detail with reference to the accompanying drawings.

BRIEF DESCRIPTION OF THE DRAWINGS

In FIG. 1, Ox−, Ox+, Hy− and Hy+ designate a group dosed with no Compound 1 under oxygen conditions, a group dosed with Compound 1 under oxygen conditions, a group of hypoxic cells dosed with no Compound 1 and a group of hypoxic cells dosed with Compound 1, respectively.

In FIG. 2, Hypoxic, Oxic, (+) and (−) mean hypoxic cells, cells under oxygen conditions, administration of Compound 1 and no administration of Compound 1.

DETAILED DESCRIPTION OF THE INVENTION AND PREFERRED EMBODIMENTS

Figure 1:
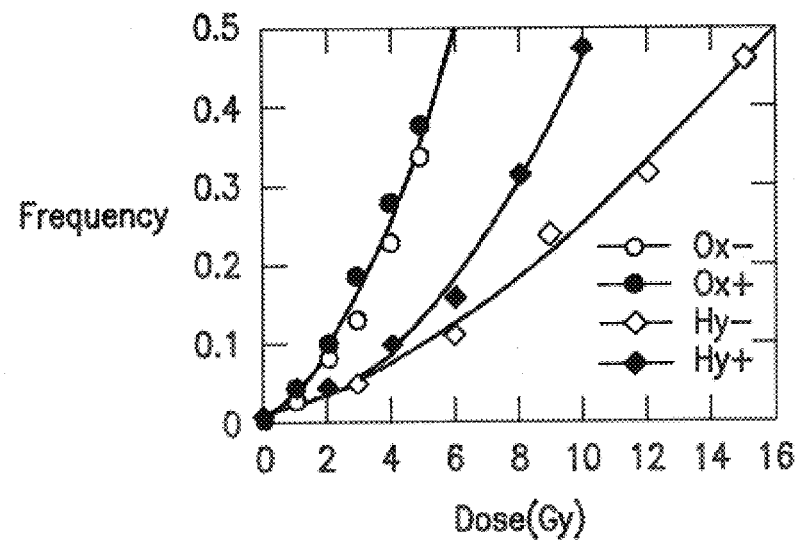
FIG. 1 diagrammatically illustrates a relationship between an irradiation dose and a proportion of apoptotic cells as to L5178Y cells.

In the general formula (1) which represents the 2-nitroimidazole derivative used in the method for inducing apoptosis of cancer cells according to the present invention, examples of the alkyl, alkenyl or alkynyl group substituted by 1–3 hydroxyl groups represented by R include those having 1–6 carbon atoms. Those having 3–6 carbon atoms are preferred. Examples of preferable compounds include 1-(2,3-dihydroxy-1-(hydroxymethyl)-propoxymethyl)-2-nitroimidazole (Compound 1), 1-(4-hydroxy-2-butenyloxymethyl)-2-nitroimidazole (Compound 2) and 1-(2,3-dihydroxypropoxymethyl)-2-nitroimidazole (Compound 3). Of these, Compound 1 is particularly preferred in that it has low neurotoxicity.

These compounds can be prepared by condensing 2-nitroimidazole and acyloxymethoxypoly(mono) acyloxyalkyl (alkenyl) in the presence of a Lewis acid and then deblocking an acyl group from the resultant condensate.

As described in Example which will be described subsequently, the 2-nitroimidazole derivative (1) has an excellent effect for inducing apoptosis of cancer cells and is hence useful in treating cancers. However, these apoptosis-inducing agents are used in combination with other means for killing cancer cells, whereby their therapeutic effect on the cancers can be more enhanced.

Preferable examples of such means for killing the cancer cells include hyperthermia in which a high fever is induced, chemotherapy with anticancer agents, such as anticancer antibiotics such as platinum compounds such as cisplatin, fluorinated pyrimidine derivatives such as 5-FU and Futraful, mitomycin, and adriamycin, and radiotherapy by corpuscular rays and X-rays. Of these, the radiotherapy and/or the treatment with the anticancer agents are more preferred, with the radiotherapy being particularly preferred.

In addition, since the apoptosis-inducing agents according to the present invention enhance the effects of these means for killing the cancer cells, it is also possible to use the means for killing the cancer cells to a weaker extent or in a less amount than usual taking the physical strength of a patient, and the like into consideration, thereby lessening the influence of the means for killing the cancer cells on normal cells.

Incidentally, it is only necessary to administer the apoptosis-inducing agent according to the present invention at the same time as the means for killing the cancer cells is performed, or before or after that.

The 2-nitroimidazole derivatives (1), which are apoptosis-inducing agents according to the present invention, may be used either singly or in any combination thereof. With respect to the dose of the apoptosis-inducing agent according to the present invention in the treatment of a cancer, it is only necessary to administer the agent in a proportion of 100–1,000 mg per day for an adult either at once or in several installments. The dose varies according to the kind of the means for killing the cancer cells used in combination and the diseased conditions of a patient to be dosed.

Examples of methods for administering the apoptosis-inducing agent according to the present invention include oral administration in the form of tablets, powder, granules or capsules; intravenous, intra-arterial, intraportal, subcutaneous, intracutaneous, intramusclar or intraperitoneal administration by injection or drip infusion, and intrarectal administration in the form of a suppository. Of these, the intravenous administration by injection or drip infusion is preferred because the compound represented by the general formula (1) is metabolized faster.

According to such an administration route, the apoptosis-inducing agent according to the present invention may be administered together with optional ingredients for forming a preparation suitable for the administration route. Examples of such optional ingredients include excipients such as crystalline cellulose, binders such as hydroxypropylmethyl cellulose, coating agents such as hydroxypropylmethyl cellulose and terephthalate thereof, lubricants such as zinc stearate and aluminum stearate, sugar-coating agents such as sucrose and maltitol, disintegrators such as starch, extenders, taste and smell corrigents, emulsifying, solubilizing and dispersing agents such as polyoxyethylene hardened castor oil, stabilizers, pH adjusters, and isotonicity-imparting agents.

The apoptosis-inducing agent according to the present invention administered in this manner facilitates the apoptosis of cancer cells by using it in combination with the means for killing the cancer cells as described in the Example and can hence enhance the therapeutic effects of such a means on cancers.

The present invention will hereinafter be described by the following Example. However, the present invention is not limited in any way by this example.

Example 1

After L5178Y cells were cultured in an RPMI 1640 medium added with 10% FBS, the cells were collected by centrifugation and diluted to $2 \times 10^5$ cells/ml. The diluted solution was placed in an amount of 5 ml in a glass Petri dish 3 cm in diameter. Oxygen in the Petri dish was purged by causing an oxygen-free gas containing 95% of nitrogen and 5% of carbon dioxide to flow at a rate of 1,000 ml/min in an airtight irradiation container to prepare radio-resistant hypoxic cells. The cells were irradiated with radiation (X-rays) in various doses under conditions that 1 mM Compound 1 was or was not added. After the thus-treated cell samples were then cultured for 48 hours, Hoechst 33342 was added to the samples to count the number of chromatin agglutinated apoptotic cells. The results are illustrated in FIG. 1 together with the results in the case where the irradiation was performed under oxygen (aerobic) conditions. Under the oxygen conditions, the cells were induced to apoptosis irrespective of the presence of Compound 1. On the other hand, the hypoxic cells are prevented from being induced to apoptosis when Compound 1 was not present. Accordingly, it is understood that the radioresistant hypoxic cells are induced to apoptosis by adding Compound 1 to them.

Figure 2:
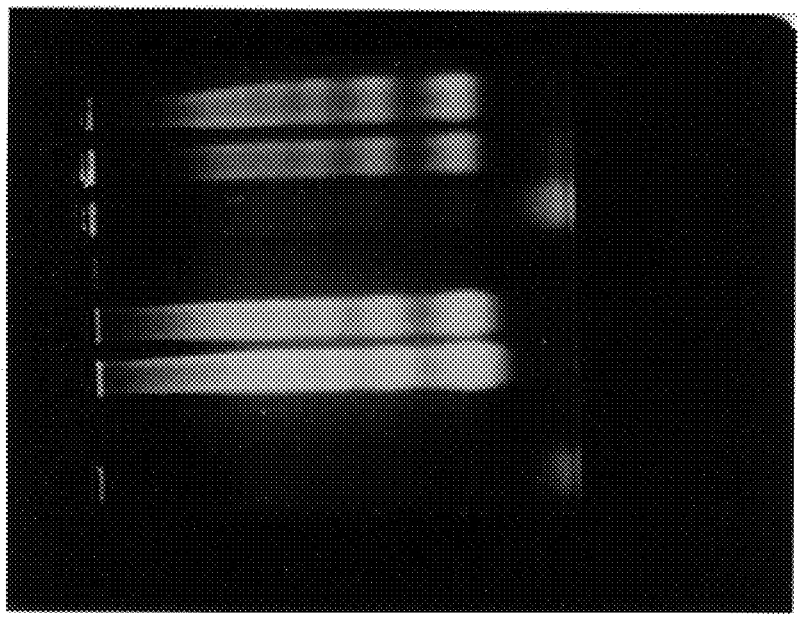
FIG. 2 illustrates agarose gel electropherograms of DNAs extracted from irradiated (5 Gy) and unirradiated (0 Gy) cells.

DNAs were extracted from cells treated with 0 Gy and 5 Gy, among the irradiated cells, and subjected to agarose gel electrophoresis. The results are illustrated in FIG. 2. As apparent from FIG. 2, it is understood that a ladder structure characteristic of apoptosis is not recognized irrespective of the presence of oxygen and Compound 1 when no irradiation was performed, while the ladder structure is recognized when the irradiation was performed.

Figure 3:
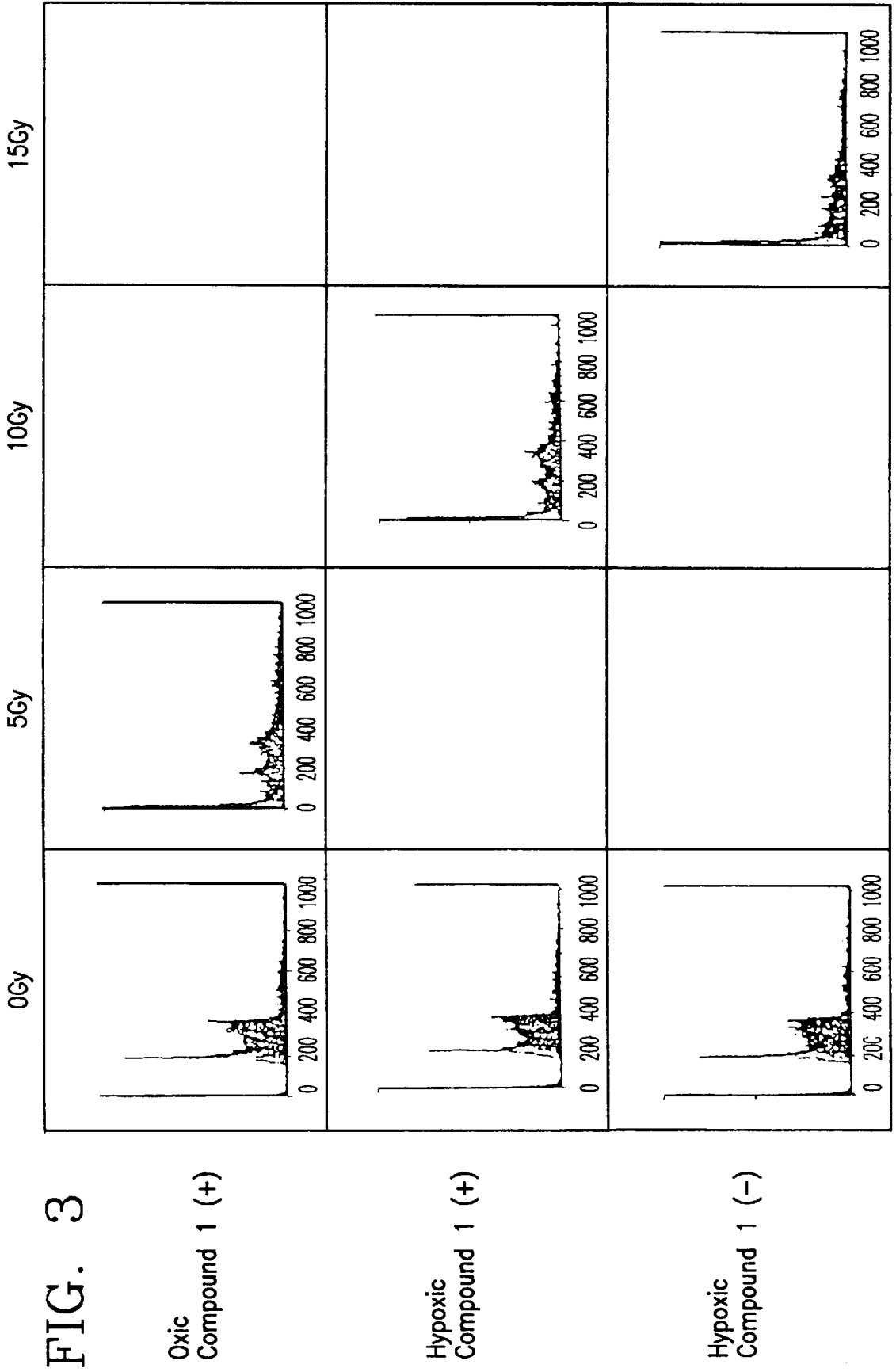
FIG. 3 illustrates results obtained by determining the formation of apoptotic corpuscles as changes in DNA content by flow cytometry.

With respect to these cells, the formation of apoptotic corpuscles was determined as changes in DNA content by flow cytometry. The results are illustrated in FIG. 3. It is understood from the results that the addition of 1 mM Compound 1 to the radioresistant hypoxic cells can bring about the same apoptosis-inducing effect the case of 15 Gy irradiation without adding Compound 1 even in 10 Gy irradiation. Accordingly, the addition of Compound 1 can reduce the irradiation dose required of treatment for cancers to two thirds.

What is claimed is:

1. A method for inducing apoptosis of cancer cells which are treatable by hyperthermia or chemotherapy in a patient in need thereof which comprises administering to said patient an ehancing effective amount of a 2-nitroimidazole derivative selected from the group consisting of 1-(2,3-dihydroxy-1-(hydroxymethyl)-propoxymethyl)-2nitroimidazole, 1-(4-hydroxy-2-butenyloxymethyl)-2-nitroimidazole and 1-(2,3-dihydroxypropoxymethyl)-2-nitroimidazole; said method being used in combination with an effective amount of hyperthermia or chemotherapy.

2. Method for treating cancers which are treatable by hyperthermia or chemotherapy in a patient in need thereof, which comprises adminstering to said patient subjecting cancer cells of said cancer to an effective amount of a chemotherapeutic agent or hyperthermia and an enhancing effective amount of a 2-nitroimidazole compound so that said selected from the group consisting of 1-(2,3-dihydroxy-1-(hydroxymethyl)-propoxymethyl)-2-nitroimidazole, 1-(4-hydroxy-2-butenyloxymethyl)-2-nitroimidazole and 1-(2,3-dihydroxypropoxymethyl)-2-nitroimidizole.

3. The method of claim 2 wherein said 2-nitroimidazole compound is administered in an amount of 100–1000 mg per day.

4. The method of claim 2 wherein the cancer cells are subjected to said hyperthermia.

5. The method of claim 2 wherein said cancer cells are subjected to a chemotherapeutic agent.

6. The method of claim 5 wherein said chemotherapeutic agent is selected from the group consisting of cisplatin, 5-fluorouracil, futraful, mitomycin and adriamycin, and said cancer is limited to cancers which respond to treatment with said chemotherapeutic agent.

* * * * *

UNITED STATES PATENT AND TRADEMARK OFFICE
CERTIFICATE OF CORRECTION

PATENT NO.   : 5,929,104
DATED        : July 27, 1999
INVENTOR(S)  : Harumi Ohyama, Takeshi Yamada, Yoshiya Furusawa, Atsuko Kamohara and Mizuho Saito It is certified that error appears in the above-identified patent and that said Letters Patent is hereby corrected as shown below:

Column 4,
Line 53, cancel "subjecting".
Line 54, cancel "cancer cells of said cancer".
Line 56, cancel "so that".
Line 57, cancel "said".

Signed and Sealed this

Sixth Day of August, 2002

Attest:

Attesting Officer

JAMES E. ROGAN
Director of the United States Patent and Trademark Office